United States Patent
Kober et al.

(10) Patent No.: US 7,950,270 B2
(45) Date of Patent: May 31, 2011

(54) METHOD AND DEVICE FOR DETECTING VOLATILE ANALYTES IN AIR SAMPLES

(76) Inventors: Reiner Kober, Fussgönheim (DE); Thomas Christen, Dannstadt (DE); Erich Probeck, Bockenheim (DE); Joachim Bargon, Bonn (DE); Fritz Vögtle, Alfter-Impekoven (DE); Gerhard Horner, München (DE)

(*) Notice: Subject to any disclaimer, the term of this patent is extended or adjusted under 35 U.S.C. 154(b) by 593 days.

(21) Appl. No.: 10/554,591

(22) PCT Filed: Apr. 26, 2004

(86) PCT No.: PCT/EP2004/004401
§ 371 (c)(1),
(2), (4) Date: May 14, 2007

(87) PCT Pub. No.: WO2004/097390
PCT Pub. Date: Nov. 11, 2004

(65) Prior Publication Data
US 2008/0105029 A1    May 8, 2008

(30) Foreign Application Priority Data
Apr. 26, 2003    (DE) .................................. 103 18 956

(51) Int. Cl.
*G01N 7/00* (2006.01)
(52) U.S. Cl. .................................................. 73/31.01
(58) Field of Classification Search .............. 73/31.01; 436/149
See application file for complete search history.

(56) References Cited

U.S. PATENT DOCUMENTS

| | | | | |
|---|---|---|---|---|
| 4,399,225 A | * | 8/1983 | Hansen et al. | 436/34 |
| 4,895,017 A | * | 1/1990 | Pyke et al. | 73/24.06 |
| 5,283,711 A | * | 2/1994 | Schmitz | 361/286 |
| 6,156,578 A | * | 12/2000 | Tom | 436/149 |
| 6,257,049 B1 | * | 7/2001 | Greybush | 73/29.01 |
| 6,405,135 B1 | * | 6/2002 | Adriany et al. | 702/5 |
| 6,556,943 B2 | * | 4/2003 | Kuwahara et al. | 702/115 |
| 6,931,913 B2 | * | 8/2005 | Manoosingh | 73/31.01 |
| 2004/0079651 A1 | | 4/2004 | Kober et al. | |

FOREIGN PATENT DOCUMENTS
EP    0 878 711 A1    11/1998
WO    WO 02/068953 A1    9/2002

OTHER PUBLICATIONS

Rösler et al., Sensor System for the Detection of Organic Pollutants in Water by Thickness Sheer Mode Resonators, Sensors and Actuators B, 48; pp. 415-424, 1998.
Frank Jay Ed., IEEE Standard Dictionary of Electrical Terms, IEEE and Wiley-Interscience, New York, pp. 782-784, 1997.
Li et al., Surface Acoustic Wave Microsensors based on Cyclodextrin Coatings, Sensors and Actuators B, 69; pp. 75-84, 2000.

* cited by examiner

*Primary Examiner* — Hezron Williams
*Assistant Examiner* — Alex Devito
(74) *Attorney, Agent, or Firm* — Novak Druce + Quigg LLP (57) ABSTRACT

The invention relates to a method and a device (16) for detecting volatile analytes in air samples, where a masssensitive sensor (20) with at least one sensor area (21) which is equipped with a surface layer with selective sensitivity for the analyte(s) to be detected is brought into contact with the air sample to be analyzed, the mass change of the surface layer is detected in the form of electrical signals and the electrical signals are evaluated. It is provided in accordance with the invention that the sensor signal is already evaluated at a point in time at which the maximum sensor signal for the analyte concentration in question is not yet obtained.

21 Claims, 2 Drawing Sheets

METHOD AND DEVICE FOR DETECTING VOLATILE ANALYTES IN AIR SAMPLES

The invention relates to a method and a device for detecting volatile analytes in air samples, in particular to a method and a device for detecting volatile substances, in particular fumigants from soil samples.

The applicant's international patent application WO 02/068953, which is herewith expressly incorporated in its entirety, discloses a method and a device for detecting soil fumigants by analyzing air from a soil sample.

The soils used in agriculture or in horticultural establishments can be infected with plant-injurious organisms, also known as phytopathogens, such as nematodes, soil-dwelling insects, germinating plants, soil bacteria or soil fungi. Frequently, it is therefore necessary to disinfest agriculturally used soils prior to the next planting or replanting, for example by treatment with a fungicide or a nematicide. Soil disinfestation is in most cases carried out using what are known as fumigants (smoke generators or gas-generating products for the soil). Fumigants are conventionally applied in liquid form or in solid form. While liquid formulations act in the soil owing to their high vapor pressure, solid compounds, which are introduced into the soil for example in the form of granules, disintegrate as the result of the soil moisture to give gaseous, biocidally active compounds. The preparations diffuse through the capillary system of the soil, where they meet the pests in the form of a respiratory poison. When coming into direct contact, fumigants may also act as contact poisons. A large number of modern soil disinfestants such as, for example, the applicant's dazomet granules BASAMID®, release, upon use, methyl isothiocyanate (MITC), of the formula Me—N=C=S, as the actual biologically active agent. Other fumigants release halogenated hydrocarbon such as 1,3-dichloropropene or bromomethane as biologically active agent. Owing to the phytotoxic activity of these substances, tests as to whether the active substance still remains in the soil are carried out prior to planting. To date, this was done using what is known as the cress test (germination test), since cress reacts highly sensitively to the nematicides. However, this test is relatively complicated and time-consuming.

WO 02/068953 describes a portable analyzer for detecting soil fumigants such as MITC, which is simple to operate, yields rapid and reliable results and therefore appears as a promising alternative to the cress test. The apparatus described in this document comprises detection means which, upon contact with the air sample, generate electrical signals which depend on the concentration in the air sample of the fumigants to be detected. To this end, the detection means comprise at least one mass-sensitive sensor which comprises suitable surface layers which have selective sensitivity for the fumigants to be detected.

Mass-sensitive sensors are, for example, what are known as "quartz micro-balances" (QMB) or as "surface-acoustic wave devices" (SAW). Quartz micro-balances are employed for example in coating plants, for example in sputter plants, for controlling the thickness of the coating. Usually, a quartz oscillator is integrated into an electrical resonant circuit. The quartz crystal makes contact with metallic electrodes and, exploiting the reverse piezo-electrical effect, is stimulated with a frequency which is typically in the radio frequency range and which corresponds to a mechanical resonant frequency of the quartz. This results in the stimulation of sympathetic vibrations, which fix a stable oscillation frequency of the resonant circuit. The frequency of resonance depends on the mass of the quartz oscillator, so that mass changes, for example caused by adsorption or absorption of a substance to be detected, can be detected as changes in the frequency of resonance. Electrical bridge circuits can be used to measure frequency changes in the order of 1 Hz.

The sensor is provided with a coating which is as selectively sensitive as possible for the analyte to be detected, for example MITC. In the ideal case, a single sensor with a highly specific coating would therefore suffice for detecting the substance in question. However, air samples such as, for example, soil air from the agricultural sector, comprise a multiplicity of different substances. In addition to the gases present in the atmospheric air, increased $CO_2$ contents (typically 0.3 to 3.0, but in some cases also up to 10% by volume) are found in the soil air, mainly owing to the microbially-caused degradation of degradable organic substances. Besides, other gases are also formed in soils, mainly owing to microbial processes. Depending on the substances present, and the Eh-pH conditions of the different soils, which vary depending on the season, these gases may be, for example, $N_2O$, $NO$, $NO_2$, $NH_3$, $SO_2$, $H_2S$, $CH_4$, $C_2H_4$, and other substances with a relatively high vapor pressure. Moreover, depending on the load of the ambient air and of the soils with the presence of volatile organic compounds such as fuels, solvents and similar from anthropogenic sources must be expected in the soil air. Thus, tetrachloroethylene contents in the soil air of 0.1 to 112 $mg/m^3$ and similarly increased trichloroethene and trichlorethane contents were measured approximately 15 years ago even in largely unpolluted soils of south Germany.

Coated mass-sensitive sensors usually display a more or less pronounced sensitivity for individual, but usually several, components of a gas mixture. Chemosensors frequently also respond with similar sensitivity to substances which are related in type owing to what is known as "cross-sensitivities". This is why in most cases a plurality of sensor areas in suitable combinations, known as sensor arrays, are required for distinguishing, or unambiguously detecting, even a single chemical compound. Such systems, which are based on a wide range of chemosensory measuring principles, have already been described in the literature for other applications than the detection of fumigants as what are known as "electronic noses". In accordance with WO 02/068953, this is why it is preferred to use a plurality of sensors which are preferably coated with different selective layers. In principle, the more unspecific the coatings of the individual sensors for the substances to be detected, and the broader the field of application of the sensor array, the more sensors will be required.

The liquid-stationary coating materials for mass-sensitive sensors which are known from the what are known as chemical noses, such as, for example, polymer and in particular silicone coatings, prove to be unsuitable for highly sensitive measurements since the viscous mass causes great damping of the oscillator quartz. Other detection techniques such as, for example, the use of conductivity sensors, frequently fail in practice since the sensor material need not only to be compatible with the analyte to be detected, but also to show the desired physical effect, that is to say, for example, a change in conductivity, upon adsorption of the analyte. WO 02/068953 therefore proposes to coat the mass-sensitive sensor of the detection system with macrocycles and/or dendrimers. Such coatings have already been described for example for the gravimetric detection of solvent vapors in Ehlen et al., *Angew. Chem., Int. Ed. English* 32, 111-112 (1993). Furthermore, such selective coatings were used for the detection of carbonyl compounds in the gas phase, and of ammonia.

While the detection system described in WO 02/068953 has proved itself successfully, enhancement modules must generally be arranged upstream of the actual sensor unit in order to achieve the sensitivities required in practice, for example when detecting MITC. While an increased layer thickness of the selective coatings would also be accompanied by a higher sensitivity since correspondingly more adsorption sites are then available to the analytes, this leads to extremely long measuring times until a stationary signal is achieved, which, again, cannot be tolerated in practical use. A broader use of the sensor system for detecting volatile analytes other than fumigants is not mentioned in this document.

The present invention is therefore based on the object of providing a method for detecting volatile analytes in air samples which is capable of determining the concentration of the analytes in air samples to be detected within as short as possible a measuring time with high sensitivity and accuracy. The method according to the invention is to be carried out in particular in a small portable apparatus. Carrying out the method according to the invention with the apparatus according to the invention is to be so simple and reliable a procedure that no or only minimal training of the user is required. The method according to the invention and the corresponding device are to be highly flexible in design so that they can be adapted readily to the detection of a wide range of volatile analytes.

This object is achieved by the method in accordance with the present claim 1. Advantageous developments of the method according to the invention are subject-matter of the dependent claims.

Accordingly, the invention relates to a method for detecting volatile analytes in air samples, where a mass-sensitive sensor with at least one sensor area which is equipped with a surface layer with selective sensitivity for the analyte(s) to be detected is brought into contact with the air sample to be analyzed, the mass change of the surface layer is detected in the form of electrical signals and the electrical signals are evaluated, where the sensor signal is evaluated at a point in time at which the maximum sensor signal is not yet obtained.

The method according to the invention is based on the observation that the signal intensity during the analysis of an air sample, after the sensor has been brought into contact with the air sample to be analyzed, shows, as a rule, an exponential curve so that relatively soon after bringing the sensor into contact with the sample as much as approximately 80 to 90 percent of the later maximum signal intensity are obtained while the final adjustment of the accumulated signal value takes considerably longer. The measuring time can therefore be shortened considerably owing to the dynamic measuring method which has been proposed in accordance with the invention, where the measured signal is already detected in the build-up phase.

In the present connection, volatile analytes are understood as meaning any nonair substances which may be present in air samples, depending on the field of application.

The sensor signal is preferably evaluated at a point in time at which between 50 and 99%, preferably between 70 and 90% and especially preferably approximately 80 to 85% of the maximum sensor signal are obtained. By calibrating the sensor for a particular analyte, the time of measurement after bringing the sensor into contact with the air sample which corresponds to, for example, 90% of the sensor signal ($t_{90}$ value) can be determined. If the point in time of bringing the sensor into contact with the air sample to be analyzed and the point in time of measurement are controlled accurately, the $t_{90}$ value can be measured with the same reproducibility as the accumulated signal value, which is obtained much later. The $t_{90}$ value can then even be used for carrying out absolute concentration measurements by corresponding calibration for the analyte in question. Typical gas contact times up to the data registration are 1 to 60 minutes, preferably 5 to 30 minutes. In comparison, measuring times in the order of hours are required for measuring the maximum sensor signal.

To obtain a more favorable signal-noise ratio, an additional, short measuring interval can be defined once the predetermined time of measurement has been reached, over which interval the mean of the sensor signals, which are still climbing slightly at this point in time, is taken.

After each measurement, the mass-sensitive sensor is advantageously purged with a purge gas to allow the desorption of the analytes which have accumulated on the surface layer or in the layer. Purging with the gas takes place immediately after the time of measurement or the short measuring interval. Owing to the dynamic recording of the signal prior to reaching the accumulated signal value, the time required in the purge phase until the sensor signal has returned to the initial level is reduced drastically. The sensor thus takes considerably less time to be ready for a new measurement. The mass-sensitive sensor is therefore preferably purged with a purge gas immediately prior to each measurement.

A suitable purge gas is, for example, any inert gas which is available in as pure a form as possible at a reasonable price. An example of a preferred purge gas is therefore nitrogen.

However, in accordance with an especially preferred variant of the method according to the invention, the purge gas used for the mass-sensitive sensor is ambient air, which can be delivered for example by a small pump or a blower. This allows the realization of a particularly small and handy instrument which requires no integrated purge gas store or no connections for an external purge gas store.

Using the method according to the invention, air samples can be analyzed directly. However, it is also possible to detect volatile analytes from solid or liquid sample materials. To this end, the sample material is advantageously arranged in a sample container, where a concentration equilibrium of the analyte concentration between the sample material and the air in the sample container establishes so that, once the equilibrium phase has elapsed, the analyte can be detected in the air taken from the sample container.

A large number of the selective surface layers preferably used in the method according to the invention are moisture-sensitive. This problem arises in particular in the case of those surface layers which are sensitive for the detection of polar analytes. To suppress the moisture sensitivity of the sensors, it is proposed in accordance with the invention that the humidity content of the air sample comprising the analyte to be detected corresponds to the humidity content of the ambient air used as purge gas. This can be achieved for example by enclosing a sample material to be analyzed in a container which is impermeable for water vapor and permeable for the analyte(s) to be detected. The sealed container, which is filled with the sample material, is arranged in a sample container filled with ambient air. The sample container is likewise sealed, and a certain time is allowed to elapse until an equilibrium concentration of the volatile analyte between the sample material to be analyzed and the air sample surrounding the container. Owing to the use of the water-vapor-impermeable film, the atmospheric humidity of the air sample in the sample container is unchanged and continues to correspond to the atmospheric humidity of the ambient air. Thereafter, the air sample from the sample container is analyzed. The results obtained are virtually independent of the actual atmospheric humidity of the ambient air at the time of measurement. Suitable containers, which are impermeable for moisture, but permeable for a large number of analytes to be detected, are, for example, bags made of a plastic material. Such bags especially preferably consist of, for example, an HDPE film (HDPE=high density polyethylene) with a wall thickness of 10-25 μm, preferably 15-20 μm. In particular, an HDPE film with a wall thickness of approx. 16 μm has proven useful for detecting soil fumigants such as MITC. Depending on the analyte, however, LDPE films with a typical wall thickness of 10 to 15 μm may also be used. The terms "permeable" and "impermeable" are, of course, to be understood in the relative sense in the present context. Thus, the container is moisture-impermeable in the present context when the time constant for the diffusion of water vapor substantially exceeds the time constant for the diffusion of the analyte to be detected.

As an alternative, or in addition, to the above-described compensation of the sensors' moisture sensitivity, it is possible to employ, in the method according to the invention, at least one specific moisture-sensitive sensor, besides the sensors which are sensitive to the analyte(s) to be detected, so that the humidity content of the air sample can also be determined. The analyte concentrations measured can then be corrected via the atmospheric humidity determined. It is preferred to use a commercially available capacitive sensor as humidity sensor. However, it is also possible to coat a sensor area of the mass-sensitive sensor with a material with selective sensitivity for water ($H_2O$).

The mass-sensitive sensor is preferably brought into contact with the air sample to be analyzed in what is known the stop-flow method. Here, the air sample can be taken from a sample container for example using a pump which, in order to reduce dead volumes, is preferably arranged behind a measuring chamber comprising the mass-sensitive sensor. After a brief period, the pump is stopped. Owing to the defined gas flow via the pump and accurate process control, the amount of the gas sample taken is defined, which ensures that the maximum analyte concentration from the gas phase of the sample container is available, during the measuring process, for measuring the sensor equilibrium in the measuring chamber. In this way, measurements can be carried out using a minimal volume of the air sample, so that the concentration equilibrium, of the volatile analyte to be detected, between the sample material and the surrounding air is disturbed as little as possible when taking the air sample from the sample container.

In accordance with an advantageous variant of the method according to the invention, the mass-sensitive sensor is maintained at an essentially constant temperature during operation. In this context, it is particularly advantageous to carry out not only the measurement, but also the subsequent purge phase, at an essentially constant temperature. Time-consuming heating and cooling phases are thereby dispensed with, so that expansive measurement series can be carried out in substantially less time. The preferred temperature at which the mass-sensitive sensor is maintained, is between 20 and 100° C., especially preferably between 30 and 60° C. and in particular more than 40° C. The latter case ensures that standardized and validated measuring programs can be provided for a wide range of climatic regions and use conditions. Moreover, the fact that the adsorption and desorption processes of the analyte at the mass-sensitive layers are temperature-dependent and generally proceed more rapidly at elevated temperature additionally proves to be advantageous.

The method according to the invention is suitable for detecting all inorganic and organic volatile substances whose partial pressure suffices for bringing about analyte concentrations in the ambient air which are capable of being measured.

These substances may, for example, take the form of a wide range of odoriferous substances or perfumes, that is to say volatile compounds which can be perceived with the sense of smell. When these volatile compounds are derived from foodstuffs, they are also referred to as aroma substances. Typical odoriferous substances or aroma substances which can be detected with the method according to the invention comprise E-2-hexenal, ethyl butyrate, ethyl 2-methylbutyrate, R-(+)- or S(-)-limonene, β-damascenone, vanillin, menthene thiol, butyric acid, ethanol, $H_2S$.

Furthermore, the method according to the invention can be used for analyzing constituents of foodstuffs, for example as determined by the state of their storage, by their origin, or as determined by their production, for example in the analysis of certain types of cheese and fruit varieties, in particular in the determination of apple aromas, where for example characteristic aldehydes or alcohols may be used as volatile analytes.

Also of importance in the field of food analysis is the detection of acrylamide using the method according to the invention. Thus, baking, cooking and (deep-)frying processes in industrial food production can be monitored continuously using the method according to the invention.

In fuel analysis, the method according to the invention can be used for example for detecting characteristic volatile organic substances such as, for example, alkanes and aromatic substances.

Materials which can be detected in the field of environmental analysis are, for example, disinfestants for the protection of stores or of buildings, such as, for example, $PH_3$ or analogous phosphides, such as, for example, magnesium phosphide, calcium phosphide, potassium phosphide or aluminum phosphide, or else sulfuryl fluoride.

However, especially preferred is the use of the method according to the invention in the analysis of soil samples, in particular in the analysis of soil samples treated with soil disinfestants. Typical soil disinfestants or fumigants which can be detected with the method according to the invention comprise MITC, methyl bromide, 1,3-dichloropropene, dimethyl disulfides, or iodomethanes.

Using the method according to the invention, volatile analytes in air samples, in particular soil fumigants, at a concentration in the range of from 0.1-1000 ppm, preferably in the range of from 1-100 ppm, can be detected rapidly, reliably and with high accuracy.

Moreover, the invention relates to a device, preferably designed as a portable hand-held unit, for detecting volatile analytes in air samples, in a particular device for carrying out the above-described detection method. The device according to the invention comprises a mass-sensitive sensor with at least one sensor area which is equipped with a surface layer with selective sensitivity for the analyte(s) to be detected, means for bringing the mass-sensitive sensor into contact with the air sample to be analyzed, such as, for example, conveyor pumps or blowers, detection means for determining the mass change of the surface layer of the sensor area, where the detection means provide a sensor signal which depends on the mass change, and control means for controlling the detection means and the means for bringing the mass-sensitive sensor into said contact. The device according to the invention comprises the control, by the control means, of the detection means in such a way that the sensor signal is detected at a point in time before the maximum sensor signal is reached.

Advantageously, the sensor signal detected at the predetermined point in time amounts to between 50% and 99%, by preference between 70% and 90% and especially preferably approximately 80% to 85% of the maximum sensor signal.

For example, the mass-sensitive sensor can comprise a surface-acoustic wave device. While changes in the mass occupation can be measured with high sensitivity using surface-acoustic wave devices, such sensors are at the same time highly temperature-sensitive so that complicated measures for thermostatting the devices must be taken. The possibility of designing the device as a small compact portable unit is advantageous for the fields of application of the device according to the invention which are especially preferred for the purposes of the present invention. In these fields of application, surface-acoustic wave devices are less suitable.

The sensor area of the mass-sensitive sensor therefore especially preferably comprises a quartz micro-balance, where the detection means comprise an electric resonant circuit in which the quartz micro-balance is arranged. As is the case with any type of sensor, a quartz micro-balance requires an effect which is capable of being measured physically and which is proportional to the parameter to be detected by the sensor. In this case, this is the piezoelectric effect, or its reversal, electrostriction. A quartz oscillator is a thin disk which is excised from a natural or synthetic quartz single crystal. Since the latter must be excited to oscillate, electrodes, mostly made of gold, are applied to the platelet excised, for example by vapor deposition. Depending on the crystallographic orientation of the quartz disk and the arrangement of the electrodes, various types of volume oscillation can be generated by applying an electrical AC voltage. The type of oscillation is influenced not only by the way the quartz disk is cut, but also by the oscillator switch used. This allows the targeted provocation of both longitudinal and transverse thickness oscillations with low excitation frequencies (<200 kHz) and thickness shear oscillations with high frequencies (1-300 MHz) as overtone oscillations. The thickness shear oscillation (transverse shear effect) (AT, BT section), with its high excitation frequency, is the most sensitive volume oscillation for mass weighing. If a quartz disk is coated with two thin gold layers, it can be excited to oscillate by applying an AC voltage. The basic frequency of the quartzes which are used by preference is in the order of magnitude of 10 MHz. The AC voltage applied excites a standing wave in the quartz, where in the case of the thickness shear oscillation, the parallel layers in the quartz are shifted relative to one another without further deformation. The resulting wavelength of the quartz plate depends on the mass and the shear module of the quartz. The connection between frequency and mass has been described in 1959 by Sauerbrey in the relationship named after him. This relationship allows the use of quartz oscillators as miniature scales with very high sensitivity.

The quartz oscillator thus constitutes a piezoelectric resonator in the electric resonant circuit. Changes in the mass occupation of the resonator lead to a shift in the resonance frequency of the resonant circuit, which can be evaluated electronically. To this end, the quartz micro-balance is provided with a surface layer with selective sensitivity for the analytes to be detected. The detectable mass increase in the surface layer, which is the result of the adsorption of volatile analytes from the air sample, is directly proportional to the sensor signal registered, i.e. the detuning of the resonant circuit.

The method according to the invention now makes it possible to apply the surface layer(s) with selective sensitivity in such a thickness that adsorption of the volatile analyte from the air sample takes place not only at the surface of the layer, but within the entire volume of the coating material. Great layer thicknesses, i.e. great volumes of coating material, drastically increase the number of adsorption sites for the analyte.

In particular volume oscillators such as the quartz micro-balance preferred in accordance with the invention, can therefore be equipped with selective surface materials with a layer thickness of several micrometers, which corresponds to coating masses of 20 kHz for excitation frequencies in the range of 10 MHz. In conventional quartz oscillator systems with such sensors, the response would deteriorate drastically since the diffusion of the analyte in the adsorbing layer would have to be taken into consideration. Moreover, the sensitive layer material might provide, for one and the same analyte, adsorption sites with different activation energies for adsorption and desorption, which would preferentially or less preferentially be occupied/liberated. This is why, with a given analyte concentration in the air sample, the maximum signal value in sensors with great layer thicknesses establishes only very slowly. However, the method according to the invention makes it possible to use firstly great layer thicknesses and secondly to keep the measuring time required very brief, since measuring already takes place before the maximum sensor signal which is possible is obtained. This is why the method according to the invention and the device according to the invention allow simultaneously very sensitive and rapid measuring.

The mass-sensitive sensor especially preferably comprises at least two sensor areas which are coated with the same selective coating material, but with different layer thicknesses. The thinner layers have a shorter response time. This is why their signal can be used from a safety aspect for controlling the means for bringing the mass-sensitive sensor into contact with the analyte so that, for example, the contacting means can be switched off briefly when a rapid, powerful resonance signal of the thin layers shows that the analytes are present in very high concentrations. An overload and damage of the mass-sensitive sensor system caused by high analyte concentrations is thus prevented efficiently. This applies in particular to reactive nonair analytes which, when present in high concentrations, can for example cause irreversible damage to the receptor surfaces of the surface layers with selective sensitivity.

Moreover, the concentration measuring range of the sensor can be increased advantageously by using sensor areas with surface layers with different thicknesses. The thicknesses of the different layers are preferably chosen in such a way that their detection sensitivities for the analytes to be detected differ by at least a factor of 10.

If one and the same sensor is to be used for detecting different volatile analytes in air samples, the mass-sensitive sensor preferably has a plurality of sensor areas which are equipped with surface layers with sensitivities for different analytes.

The device according to the invention advantageously furthermore comprises at least one sensor for determining the atmospheric humidity. In accordance with a first embodiment, the sensor for determining the atmospheric humidity is designed as an additional capacitive sensor unit. In accordance with a second embodiment, the sensor for determining atmospheric humidity is also a mass-sensitive sensor which is equipped with a surface layer with selective sensitivity for water.

In accordance with an especially preferred variant of the device according to the invention, the surface layer comprises macrocycles, dendrimers and/or calixarenes.

The invention also relates to methods and devices which comprise the individual features according to the invention, which have been described above, in any combination.

The invention is now illustrated in greater detail with reference to a use example and the appended drawings.

Figure 1:
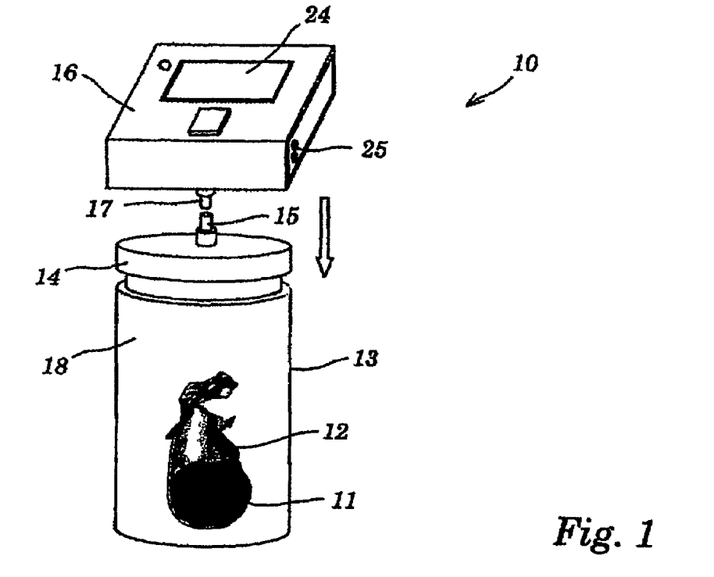
FIG. 1 shows the principle of the construction of the measuring set-up according to the invention for determining the residual content of MITC from the soil disinfestant Basamid® in a soil sample.

Referring to FIG. 1, a preferred embodiment, in total designated with the number 10, of the device according to the invention for the detection of volatile analytes in air samples can be seen, which in the case shown is employed for the detection of MITC.

A soil sample 11, which may originate for example from a field treated with Basamid®, is first removed from the soil by means of an auger which provides defined volumes of soil and introduced into a water-tight film bag 12. Between 0.01 and 5 kg, preferably 0.1 to 1 kg, of a soil sample are typically used. The film bag 12 is sealed and arranged in a sample container 13 which preferably consists of stable plastic material or of metal. Depending on the application, the volume of the sample container is between 0.1 and 2 liters, preferably between 0.5 and 1 liters. The sample container is equipped with a largely hermetically sealable, removable lid 14 which comprises a connection 15, for example a flange opening or a valve, with which the sensor device 16 according to the invention can be connected via a corresponding connection piece 17. The use of the film bag 12 has two important advantages. Firstly, the bag saves complicated cleaning of the sample container 13 and thus allows different samples to be analyzed rapidly one after the other. A second aspect of the use of the film bag is the separation of water and high amounts of water vapor from very moist or indeed wet soil samples 11. Here, the film acts as a water filter which, while being impermeable for water, permits the unhindered passage of smaller volatile organic molecules such as, for example, MITC into the sample container. Suitable film bags consist for example of HDPE (high density polyethylene) with a wall thickness in the range of from 15-25 μm. Depending on the volatile analyte to be detected in each case, the type and thickness of the film bag must naturally be adapted to the individual case to ensure that the gaseous analyte can diffuse more or less freely through the film wall.

After an adjustment or equilibratium phase of typically approximately 5 to 20 minutes, the sensor device 17 is connected to the interior of the sample container 13 via the connections 15, 17. In this context, equilibrium phase means that the MITC concentration in the gas phase 18 of the sample container, or in the film bag 12, is in equilibrium with the concentration in the soil sample 11.

Figure 2:
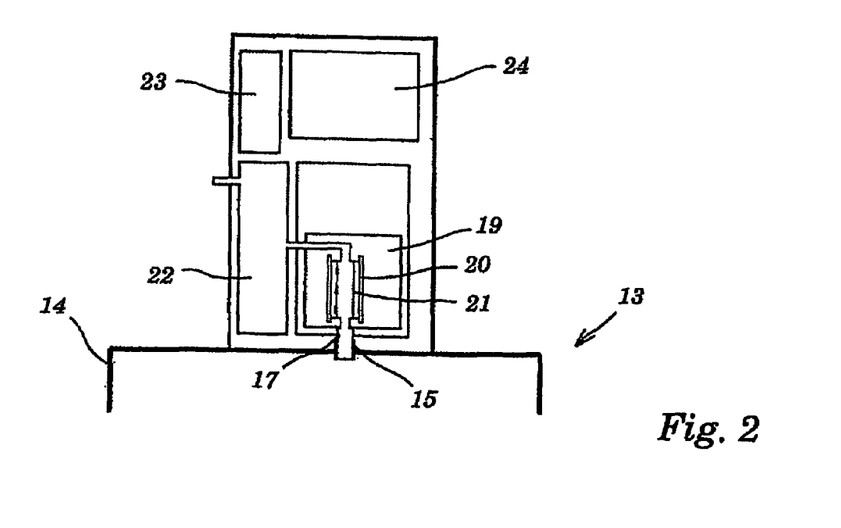
FIG. 2 shows the schematic construction of a preferred embodiment of the device according to the invention.

The construction of the sensor device 16 according to the invention is shown in more detail in FIG. 2. The sensor device 16 comprises a measuring chamber 19 in which the mass-sensitive sensor 20 is arranged. In the example shown, the sensor 20 has six different sensor areas 21 in the form of a sensor array. The MITC-sensitive sensor areas are designed as quartz micro-balances and provided with a coating of calixarenes. The sensor 20 is brought into contact with an air sample from the gas phase 18 of the sample container 13 via a pump 22 arranged downstream of the measuring chamber 19. To bring the sensor 20 into contact with ambient air, the direction of delivery of the pump 22 can be reversed. In addition, the sensor device 16 has a control and evaluation unit 23 and a display 24 for displaying the data. As can be seen from FIG. 1, the sensor device 16 can additionally be provided with connections 25 for transferring data, for example to an external electronic recording medium or a computer.

The measurement is advantageously carried out in a stop-flow mode. In this context, it is especially advantageous to use a measuring chamber of very small volume, for example to avoid unduly high dilution with incoming fresh air of the gas space of the sample container for a possible second measurement. In general, it suffices to remove a very small gas sample of a few ml, preferably from 0.1 to 5 ml, and especially preferably of approximately 1 ml. Usually, the volume of the measuring chamber, which is advantageously likewise in the 1 ml order of magnitude, is purged repeatedly with the MITC-comprising gas. By directly attaching the MITC sensor 16 to the sample container 13, the dead volumes in the gas pathways are small and negligible. The gas sample is withdrawn from the sample container 13 via the pump 22, which is arranged downstream of the measuring chamber 20 in order to further reduce dead volumes. After a brief time, the pump is stopped. The amount of the gas sample taken is defined by the defined gas flow via the pump and the accurate process control and it is ensured that the maximum MITC concentration from the gas phase of the sample container is available for the equilibrium measurement of the sensors in the measuring chamber during the entire measuring process.

The measuring chamber together with the sensors is thermostatted to for example 45° C. so that the instrument can be operated with standardized and validated measuring programs in all climates and in a wide range of external conditions.

Since the calixarene coating, which is especially preferably employed for the detection of MITC, is sensitive to humidity, the effect of humidity on the measurement is advantageously eliminated by firstly using ambient air for purging the sensors and secondly by ensuring, by using the film bag in the sample container, that ambient air is also employed as the air sample to be analyzed. Purge gas and air sample therefore have essentially the same atmospheric humidity. This method even makes it possible to substantially eliminate the effect of the atmospheric humidity which in the tropics can be more than 90% relative atmospheric humidity, on the measured result. The additional use of a humidity sensor is, however, advantageous. Suitable are generally mass-sensitive humidity sensors based on quartz resonator technology or sensors which operate as capacitive systems and which cause a change in measured resistances by changed atmospheric humidities. Such capacitive sensors are commercially available. The humidity sensors are advantageously arranged directly in the gas stream. By suitable calibration, the effect on the volatile analyte, or on the specific sensor layers, can be determined. In this manner, analytes can be identified with a relatively high accuracy of measurement. In the case of MITC, ranges of from 1-100 ppm can thus be readily measured with standard deviations of less than 20%.

Figure 3:
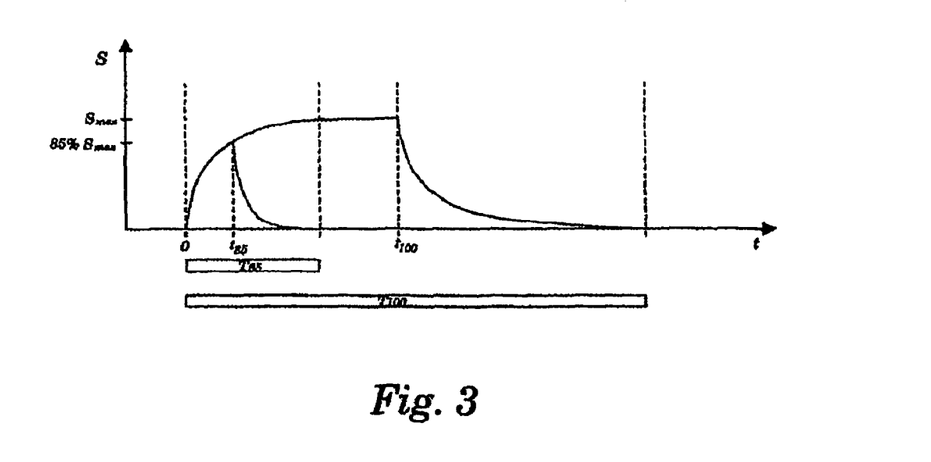
FIG. 3 shows the time curve of the sensor signal in the detection method according to the invention in comparison with a conventional detection method, where the maximum sensor signal is evaluated.

FIG. 3 shows a typical curve of a measured signal which illustrates the advantages of the measuring method according to the invention. At time t=0, the mass-sensitive sensor is brought into contact with the air sample to be analyzed. At the time $t_{85}$, the measured signal S has reached 85% of its maximum signal intensity $S_{max}$. At this point in time, the value of the signal is determined. Then, the sensor is purged with ambient air by reversing the pump so that the signal already returns to its original value after a total measuring time of $T_{85}$. In comparison, the corresponding measurement times $t_{100}$ and $T_{100}$ for measuring the maximum signal intensity at a given analyte concentration are shown in a further curve. It can be seen that the method according to the invention leads to a drastic reduction of the measuring times.

Suitable coating materials for the sensor areas of the mass-sensitive sensor are all those compounds which are capable of reversibly adsorbing certain guest substances such as, for example, MITC. The coating material should be a solid so that the material remains on the quartz even when the quartz micro-balance moves and oscillates. It should be nonvolatile and should be chemically stable and not change its state up to the desired measuring temperature.

Figure 4:
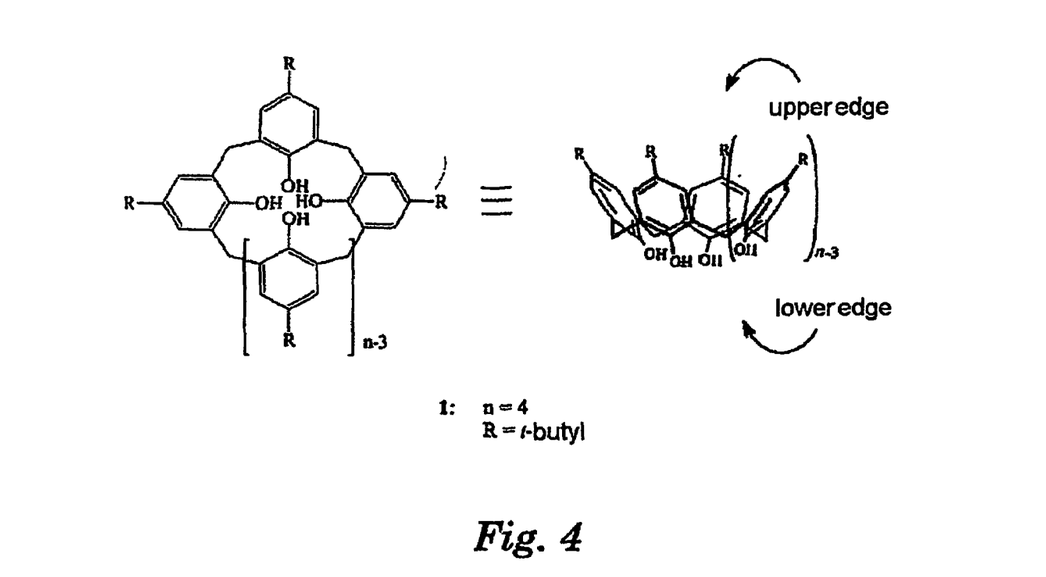
FIG. 4 shows the structure of typical calixarenes, which are preferred as coating materials of the sensor areas.

Calixarenes have proved to be especially preferred coating materials. The term calixarene is derived from the cup shape (Greek: calix=cup or vase) of the simplest representative, calix[4]arene, which is shown in FIG. 4. The general term is calix[n]arenes, where n>3).

The calixarenes belong to the metacyclophans. They can be synthesized by subjecting phenols and formaldehyde to cyclocondensation, can be functionalized in many ways and thus tailored to desired host-guest relations. By varying the number of phenol rings, it is also possible to modify the size of the internal cavity.

Owing to their ability of being able to complex neutral organic molecules and ions, they are extremely interesting as sensor layer. Moreover, they are used as selective ligands in analytical chemistry, in medical diagnostics, in the processing of nuclear waste and as enzyme mimetics.

Typical calixarenes which are suitable as coating materials are compiled in Table 1 hereinbelow.

cycles can also be assembled in the form of a modular design, as can the lactamamide macrocycles. The phenolic ether groups which are present, the p-systems of the aromatics and any further functionalities in the ring system open up a broad spectrum of host-guest interactions.

Finally, what are known as dendrimers and polyphenylenes are also suitable as coating materials. The dendrimers are monodisperse oligomeric or polymeric compounds with highly branched monomers which, however, are not crosslinked. This results in a tree-like structure which gives rise to the name (Greek: "dendron"=tree). Three parameters characterize a dendrimer. They are the generation number, the degree of branching and the type of linkage. The generation number indicates the number of monomeric fragments in a chain which are bound to the central core. The degree of branching describes the number of branchings per monomer per generation. The absolute number of monomer units results from the degree of branching to the power of the generation number. The type of linkage indicates the manner in which each generation is bound to the previous one. The class of the hyper-branched polyphenylenes is very similar to the dendrimers. They are not crosslinked but, in contrast to the dendrimers, are not monodisperse but polydisperse in design. The two parameters, viz. the number-averaged molecular mass $M_n$ and the weight-averaged molecular mass $M_w$, determine the polydispersity as the $M_w/M_n$ ratio.

Macrocycles and dendrimers which are suitable as sensor coatings are described in greater detail in the applicant's WO 02/068953.

TABLE 1

| | | | Calixarenes | |
|---|---|---|---|---|
| Name | Abbreviation | Ring size | Radical | Basic structure |
| Tert.-butylcalix[6]arene | 4C6 | 6 | t-butyl | |
| Calix[6]arene | HC6 | 6 | H | |
| Isopropylcalix[6]arene | 3C4 | 4 | i-propyl | |
| Tert.-butylcalix[8]arene | 4C8 | 8 | t-butyl | |

The novolacks, which are chemically related to the calixarenes and which are polymeric phenol/formaldehyde condensates which can be both chain-like and ring-like in structure, are also suitable as coating materials.

Other suitable coating materials are macrocycles such as, for example, lactam macrocycles or ether macrocycles. A great advantage in the synthesis of the lactam macrocycles, as is in the case of the calixarenes, is the great variety of the derivatives available. The diamine group and also the diacid chloride can be replaced readily. A further advantage of this group of substances is that the large number of functional groups gives rise to a broad spectrum of possible host-guest interactions, which means that, as a group of substances, they are candidates for forming good sensor layers. Ether macro- Drop-coating, spin-coating, airbrush or electrospray methods can be employed for coating the quartz disks with the preferred materials with selective sensitivity. The electrospray method, where the substance to be applied is dissolved in a suitable solvent which is capable of being electrically polarized, is especially preferred in this context.

The invention claimed is:
1. A method comprising
enclosing a soil sample in a first container that is impermeable to moisture and permeable to a volatile analyte;
arranging the first container in a second container that is filled with ambient air;

allowing an equilibrium concentration of the volatile analyte to be established between the soil sample and the ambient air;

purging a mass-sensitive sensor with ambient air;

subsequently, bringing the ambient air into contact with the mass-sensitive sensor comprising at least one sensor area equipped with a surface layer having selective sensitivity for the volatile analyte;

detecting a mass change on the surface layer in the form of an electrical signal from the mass-sensitive sensor after a predetermined period of time, wherein the predetermined period of time is less than an elapsed time for a calibration electrical signal from the mass-sensitive sensor to reach a maximum intensity upon exposure to the volatile analyte during a calibration; and calculating a concentration of the volatile analyte in the ambient air based on the electrical signal and a calibration measurement.

2. A method as claimed in claim 1, wherein the predetermined time is between 50 and 99% of the elapsed time.

3. A method as claimed in claim 1, further comprising
detecting at least one additional electrical signal from the mass-sensitive sensor after a second period of time that is greater than the predetermined period of time, but less than the elapsed time; and
calculating the concentration of the volatile analyte based on the mean of all the electrical signals detected after the predetermined period of time.

4. A method as claimed in claim 1, wherein the humidity content of the air sample is determined.

5. A method as claimed in claim 1, wherein the mass-sensitive sensor is brought into contact with the air sample to be analyzed in a stop-flow method.

6. A method as claimed in claim 1, wherein the mass-sensitive sensor is maintained at an essentially constant temperature during operation.

7. A method as claimed in claim 1 for detecting soil disinfectants comprising at least one of: MITC, methyl bromide, 1,3-dichloropropene, dimethyl disulfides, and iodomethanes.

8. A device for carrying out the method according to claim 1, the device comprising
a first container for enclosing a soil sample, wherein the container is impermeable to moisture and permeable to a volatile analyte;
a second container for housing the first container;
a mass-sensitive sensor having at least one sensor area, which is equipped with a surface layer with selective sensitivity for the volatile analyte;
means for purging the mass-sensitive sensor with ambient air;
means for bringing the mass-sensitive sensor into contact with an air sample to be analyzed;
detection means for determining a mass change of the surface layer of the sensor area, wherein the detection means provides a sensor signal which depends on the mass change; and
control means for controlling the detection means and the means for bringing the mass-sensitive sensor into said contact,
wherein the control means is arranged such that the sensor signal is evaluated after a predetermined period of time,
wherein the predetermined period of time is less than an elapsed time for a calibration electrical signal from the mass-sensitive sensor to reach a maximum intensity upon exposure to the volatile analyte during a calibration.

9. A device as claimed in claim 8, wherein the sensor signal detected at the predetermined point in time amounts to between 50% and 99%.

10. A device as claimed in claim 8, wherein the sensor area of the mass-sensitive sensor comprises a quartz micro-balance and the detection means comprises an electric resonant circuit in which the quartz micro-balance is arranged.

11. A device as claimed in claim 8, wherein the mass-sensitive sensor comprises at least two sensor areas, which are coated with the same material, but with different thicknesses.

12. A device as claimed in claim 8, wherein the mass-sensitive sensor exhibits sensor areas, which are equipped with layers with selectivity for different analytes.

13. A device as claimed in claim 8, wherein a humidity sensor for determining the humidity of the air sample is additionally provided.

14. A device as claimed in claim 13, wherein the humidity sensor is a separate capacitive sensor unit.

15. A device as claimed in claim 8, wherein the selective surface layer comprises a material which is selected from the group consisting of macrocycles, dendrimers, calixarenes and novolacks.

16. A device as claimed in claim 8, wherein the device is designed as a portable sensor device.

17. A method as claimed in claim 1, wherein the predetermined time is between 70 and 99% of the elapsed time.

18. A method as claimed in claim 1, wherein the predetermined time is approximately 85% of the elapsed time.

19. A device as claimed in claim 8, wherein the sensor signal detected at the predetermined point in time amounts to between 70% and 90% of the maximum.

20. A device as claimed in claim 8, wherein the sensor signal detected at the predetermined point in time amounts to approximately 80% to 85% of the maximum.

21. A device as claimed in claim 8, wherein said means for purging said mass sensitive sensor and said means for bringing the mass-sensitive sensor into contact with the air sample to be analyzed comprise a pump having a reversible direction of delivery.

* * * * *

UNITED STATES PATENT AND TRADEMARK OFFICE
CERTIFICATE OF CORRECTION

| | | |
|---|---|---|
| PATENT NO. | : 7,950,270 B2 | Page 1 of 1 |
| APPLICATION NO. | : 10/554591 | |
| DATED | : May 31, 2011 | |
| INVENTOR(S) | : Kober et al. | |

It is certified that error appears in the above-identified patent and that said Letters Patent is hereby corrected as shown below:

In Claim 9, col. 14, indicated line 17:

"50% and 99%." should read >>50% and 99% of the maximum.<<

Signed and Sealed this
Sixteenth Day of August, 2011

David J. Kappos
*Director of the United States Patent and Trademark Office*